United States Patent
Wang et al.

(10) Patent No.: US 11,602,134 B2
(45) Date of Patent: Mar. 14, 2023

(54) MOUSE MODEL OF MYOCARDITITS

(71) Applicant: PEKING UNION MEDICAL COLLEGE HOSPITAL, Beijing (CN)

(72) Inventors: Yining Wang, Beijing (CN); Chanjuan Qu, Beijing (CN); Jian Wang, Beijing (CN); Yanyu Li, Beijing (CN); Kang Zhou, Beijing (CN); Jian Cao, Beijing (CN); Lu Lin, Beijing (CN); Xiao Li, Beijing (CN); Zhengyu Jin, Beijing (CN)

(73) Assignee: PEKING UNION MEDICAL COLLEGE HOSPITAL, Beijing (CN)

( * ) Notice: Subject to any disclaimer, the term of this patent is extended or adjusted under 35 U.S.C. 154(b) by 0 days.

(21) Appl. No.: 17/571,565

(22) Filed: Jan. 10, 2022

(65) Prior Publication Data
US 2022/0361463 A1    Nov. 17, 2022

(30) Foreign Application Priority Data

May 13, 2021 (CN) .......................... 202110524213.4

(51) Int. Cl.
*A01K 67/027* (2006.01)
(52) U.S. Cl.
CPC .... *A01K 67/0275* (2013.01); *A01K 2217/052* (2013.01); *A01K 2227/105* (2013.01); *A01K 2267/0387* (2013.01)
(58) Field of Classification Search
None
See application file for complete search history.

(56) References Cited

U.S. PATENT DOCUMENTS

2019/0038713 A1    2/2019    Sobol et al.

FOREIGN PATENT DOCUMENTS

| CN | 111863259 A | 10/2020 |
| CN | 112717144 A | 4/2021 |

OTHER PUBLICATIONS

Semper (Lung Cancer, 2016, vol. 99, p. 117-119).*
Moshlehi (Lancet, 2018, vol. 391, p. 933).*
H. Semper, et al., Drug-induced myocarditis after nivolumab treatment in a patient with PDL1-negative squamous cell carcinoma of the lung, Lung Cancer, 2016, pp. 117-119, vol. 99, Elsevier.
Javid J. Moslehi, et al., Rapid increase in reporting of fatal immune checkpoint inhibitor associated myocarditis, Lancet, 2018, pp. 933, 391(10124).

* cited by examiner

*Primary Examiner* — Michael C Wilson
(74) *Attorney, Agent, or Firm* — Bayramoglu Law Offices LLC

(57) ABSTRACT

A preparation method of an anti-PD-1/PD-L1 monoclonal antibody (mAb)-induced autoimmune myocarditis model is provided, including: mediating a model with adeno-associated virus 9 (AAV9) to achieve the high expression of PDL1 in a myocardial tissue, and applying an anti-PD-1/PD-L1 mAb to the model with high PDL1 expression in the myocardial tissue for modeling. The present disclosure also provides use of an animal model prepared by the preparation method. The model prepared by the present disclosure truly simulates the pathogenesis and clinical course of autoimmune myocarditis in a patient administered with an anti-PD1/PD-L1 mAb, is close to a pathophysiological status of a clinical patient, has a high modeling rate, and can be dynamically monitored.

4 Claims, 3 Drawing Sheets

Specification includes a Sequence Listing.

MOUSE MODEL OF MYOCARDITITS

CROSS REFERENCE TO THE RELATED APPLICATIONS

This application is based upon and claims priority to Chinese application No. 202110524213.4, filed on May 13, 2021, the entire contents of which are incorporated herein by reference.

Sequence Listing

The instant application contains a Sequence Listing which has been submitted in ASCII formatvia EFS-Web and is hereby incorporated by reference in its entirety. Said ASCII copy is named GBBJHS010-PKG_Sequence_Listing, created on Jan. 10, 2022 and is 2,007 bytes in size.

TECHNICAL FIELD

The present disclosure relates to the field of biomedicine, and in particular to an anti-PD-1/PD-L1 monoclonal antibody (mAb)-induced autoimmune myocarditis model and a preparation method thereof.

BACKGROUND

As a milestone in the history of tumor immunotherapy, anti-PD-1/PD-L1 mAb is one of the highly-anticipated immune checkpoint inhibitors recently, and serves as a first-line or second-line therapeutic drug for many malignant tumors such as lung cancer and melanoma. It can significantly prolong the overall survival (OS) and the median progression-free survival (mPFS) of a patient, and shows increasing indications. However, side effects of the anti-PD-1/PD-L1 mAb are getting more and more attention, among which myocarditis is the most lethal. This is because myocarditis interferes with the normal electromechanical functions of a heart and weakens the myocardial regeneration. Once occurring, immune damage can usually be hardly repaired. Therefore, it is necessary to be highly vigilant against autoimmune myocarditis caused by tumor immunotherapy. It is stipulated that, if myocarditis occurs after the anti-PD-1/PD-L1 mAb is administered, the administration needs to be permanently stopped and a hormone and an immunosuppressant need to be immediately administered at high dosages, in which case the prognosis is still very poor. Once myocarditis occurs, a mortality rate is 40%. When the anti-PD-1/PD-L1 mAb is used in combination with an anti-CTLA-4 mAb such as ipilimumab, a mortality rate can be as high as 67%. According to literature alerts, when the anti-PD-1/PD-L1 mAb is used alone, an incidence of autoimmune myocarditis is about 6‰; and when the anti-PD-1/PD-L1 mAb is used in combination with the anti-CTLA-4 mAb, the incidence of autoimmune myocarditis increases to 3‰. However, with the increasing use of anti-PD-1/PD-L1 mAb, reports on autoimmune myocarditis have gradually increased. Due to a large number of patients with malignant tumors in China, a proportion of patients using the anti-PD-1/PD-L1 mAb has increased rapidly in recent years. Therefore, more and more patients suffer from myocarditis, and the high lethality of myocarditis has become a difficult problem in the tumor (chronic disease) management in China.

Because patients administered with the anti-PD-1/PD-L1 mAb have a low probability to undergo autoimmune myocarditis under natural conditions, the study on mechanism, early warning markers, and new treatment methods of autoimmune myocarditis depends on the successful establishment of animal models. Previous animal test results have shown that it is very difficult to successively establish models by directly administering the anti-PD-1/PD-L1 mAb. Studies such as Keynote 024 and 042 have shown that the higher the tumor proportion score (TPS) (PDL1 expression) of a tumor tissue, the better the anti-tumor effect of the anti-PD-1/PD-L1 mAb. It is mentioned in literatures that the PDL1 expression in a myocardial tissue is one of the reasons for the use of anti-PD-1/PD-L1 mAb to cause autoimmune myocarditis; and an experiment is conducted as follows: with PDL1Ig gene recombinant adenovirus as a vector, the PDL1Ig gene is transformed into Brown Norway (BN) rat dendritic cells (DCs), and then transformed DCs are infused into Lewis rats undergoing kidney transplantation, where the transfection group serves as an experimental group. Results of the experiment show that the PDL1 gene-modified DCs can significantly prolong a survival time of a transplanted kidney. It indicates that, if a myocardial tissue in a species can express PDL1 at a high level, an incidence of autoimmune myocarditis caused by the administration of anti-PD-1/PD-L1 mAb will also be greatly increased.

Adeno-associated virus (AAV) is a member of the Parvoviridae family. Members of this family are small, non-enveloped, and icosahedral viruses. These virus particles have a diameter of 20 nm to 26 nm, and includes a linear single-stranded DNA genome with a size of 4.7 kb to 6 kb. The replication and propagation of these viruses depend on the presence of a helper virus. As a gene delivery system, an AAV vector has high safety and low immunogenicity, can infect dividing and non-dividing cells, and can mediate the long-term stable expression of genes. AAV9 is a well-recognized serotype of AAV vector that efficiently and specifically expresses targeting the heart. AAV9 not only infects cardiomyocytes, but also infects other cells of the heart. The present disclosure is intended to use a cardiomyocyte-specific promoter cTNT to initiate the expression of a target gene.

At present, anti-PD-1/PD-L1 mAb-related autoimmune myocarditis is mostly reported in the safety evaluation of drug clinical trials, or in specific clinical cases, and thus there are only a few basic and clinical researches. Moreover, animal models used in the basic research are PD-1/PD-L1-knockout mouse models or mouse cardiotoxic animal models caused by combined use with radiotherapy, which show different pathogenesis, pathology, and clinical manifestations from autoimmune myocarditis caused by anti-PD-1/PD-L1 mAb in reality.

SUMMARY

The present disclosure provides a preparation method of an anti-PD-1/PD-L1 mAb-induced autoimmune myocarditis model and a model prepared thereby. The model truly simulates the pathogenesis and clinical course of autoimmune myocarditis in a patient administered with an anti-PD-1/PD-L1 mAb, is close to a pathophysiological status of a clinical patient, and has a high modeling rate, where the cardiomyopathy can be dynamically monitored through cardiac magnetic resonance.

In one aspect of the present disclosure, a preparation method of an anti-PD-1/PD-L1 mAb-induced autoimmune myocarditis model is provided, including: mediating a model with AAV9 to achieve the high expression of PDL1 in a myocardial tissue, and applying an anti-PD-1/PD-L1 mAb to the model with high PDL1 expression in the myocardial tissue for modeling.

For the preparation method described above, the model is an animal model.

The preparation method described above specifically includes the steps of:

(1) constructing a PDL1Ig gene recombinant adenovirus vector; and (2) intravenously injecting the vector constructed in step (1) into the animal model to achieve the high expression of PDL1 in a myocardial tissue of the animal model, and intraperitoneally injecting an anti-PD-1/PD-L1 mAb for modeling.

For the preparation method described above, the vector constructed in step (1) is an AAV9 vector overexpressing a gene CD274.

For the preparation method described above, the overexpression of the gene CD274 is initiated by a cardiomyocyte-specific promoter cTNT.

For the preparation method described above, the animal model is a mouse.

For the preparation method described above, the mouse is a male mouse.

The present disclosure also provides autoimmune myocarditis-associated use of the model prepared by the preparation method described above.

Beneficial Effects

In the present disclosure, PDL1 (CD274)-overexpressing AAV9 is injected into a mouse through a tail vein to achieve the high expression of PDL1 in a myocardial tissue, and then the mouse is intraperitoneally injected with an anti-PD-1/PD-L1 mAb to truly simulate the pathogenesis and clinical course of autoimmune myocarditis in a patient administered with an anti-PD-1/PDL-1 mAb. The constructed autoimmune myocarditis animal model has the advantages of high modeling rate and available dynamic monitoring, and thus can be used for clinical research on the pathogenesis, early warning markers, treatment, and the like of autoimmune myocarditis caused by the anti-PD-1/PD-L1 mAb.

DETAILED DESCRIPTION OF THE EMBODIMENTS

The following examples are intended to illustrate the present disclosure, rather than to limit the scope of the present disclosure. Unless otherwise specified, the technical means used in the examples are conventional means well known to those skilled in the art. Unless otherwise specified, the reagents and biological materials are all commercially available.

Example 1 Construction of a PDL1Ig Gene Recombinant Adenovirus Vector

I. The main process of vector construction was as follows:

1. A corresponding vector was selected, and polymerase chain reaction (PCR) primers were designed for a target fragment.

Specific primer sequences used were as follows in Table 1:

TABLE 1

| AAV-m-CD274-Nhe/Nhe-F (SEQ ID NO: 2) | ttaatacgactcactataggctagc GCCACCATGAGGATATTTGC |
|---|---|
| AAV-m-CD274-Nhe/Nhe-R (SEQ ID NO: 3) | ccttgtagtcaagcttggtgctagc CGTCTCCTCGAATTGTGTAT |

2. An appropriate restriction endonuclease was selected to digest the vector, and a purified linearized vector was recovered through agarose gel.

Reagents in the table below were added in sequence, and a resulting mixture was gently pipetted up and down for thorough mixing and then placed in a 37° C. water bath to allow a reaction for 1 h to 2 h. After the digestion was completed, agarose gel electrophoresis was conducted to recover the target fragment.

A vector digestion system was as follows Table 2:

TABLE 2

| Reagent | Volume (μL) |
|---|---|
| Vector DNA ( 1 ug/uL) | 1 |
| 10 × buffer | 4 |
| DdH$_2$O | 32 |
| NheI | 1.5 |
| NheI | 1.5 |
| total | 40 |

Notes: An amount of the restriction endonuclease used and a time of the digestion can be adjusted according to the enzyme activity; and if single-enzyme digestion is adopted, a corresponding system is adjusted.

3. PCR was conducted for the target fragment according to the designed primers, and then the target fragment with a correct size was recovered through agarose gel.

4. The linearized vector and the target fragment were ligated according to a method of homologous recombination or T4 ligation.

5. A ligation product was transformed into competent DH5a or stbl3, and a resulting bacterial solution was plated and cultivated for 12 h to 16 h.

6. Single clones were picked for colony verification.

7. Verified positive clones were selected for sequencing.

8. Plasmid extraction was conducted on a cloning sample with a correct sequence.

II. Information of the constructed vector and target gene

Figure 1:
FIG. 1 is a map of the pHBAAV-TNT-3flag-P2A-EGFP (lsz) vector carrying a target gene constructed in step 1 of an example of the present disclosure.
Figure 2:
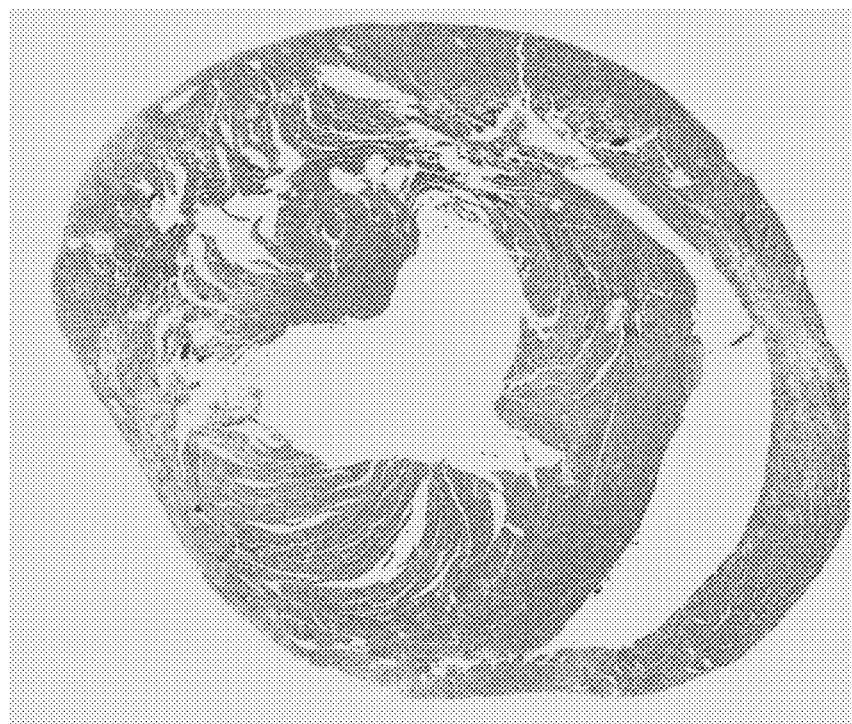
FIG. 2 shows a hematoxylin-eosin (RE) staining and CD3 immunohistochemistry result of a mouse cardiomyocyte pathological section in group A in an example of the present disclosure, where it can be seen that myofilaments of cardiomyocytes are lysed, macrophages are increased, T cells are infiltrated, and giant cells are present.
Figure 3:
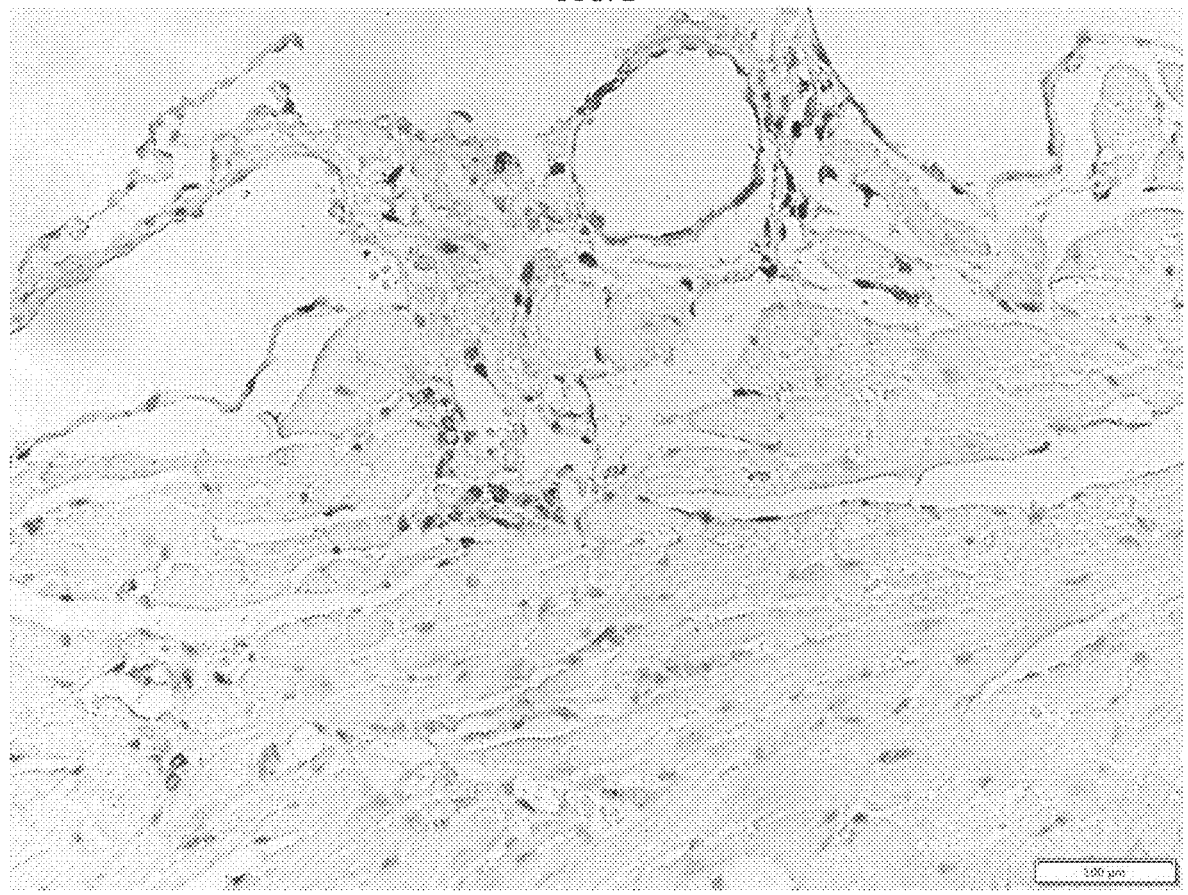
FIG. 3 shows an HE staining and CD3 immunohistochemistry result of a mouse cardiomyocyte pathological section in group A in an example of the present disclosure, which further illustrates the T cell infiltration.
Figure 4:
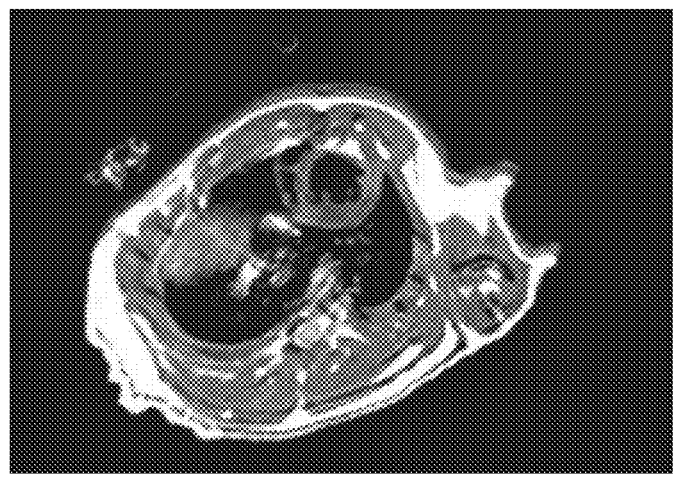
FIG. 4 shows a long T2 signal of a T2 weighted image of mouse cardiac magnetic resonance in group A in an example of the present disclosure.
Figure 5:
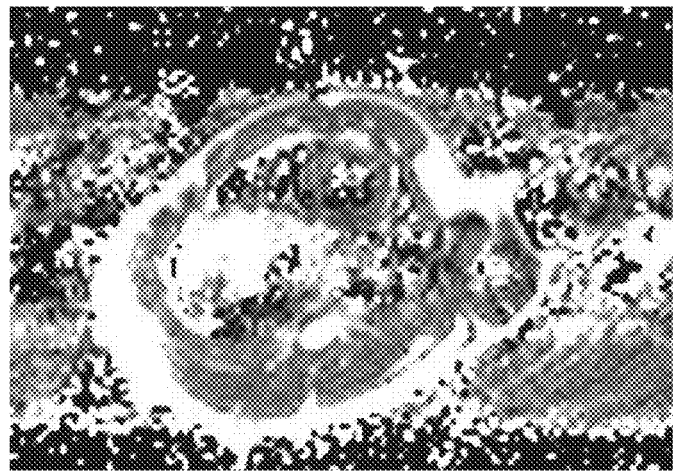
FIG. 5 shows a T2 mapping value increase of mouse cardiac magnetic resonance in group A in an example of the present disclosure.

A map of the pHBAAV-TNT-3flag-P2A-EGFP (lsz) vector carrying a target gene constructed in step 1 of this example is shown in FIG. 1. A sequence of the target gene is shown in SEQ ID NO: 1.

Example 2 Transfection of Mice to Construct Models

2.1 Experimental Mice

In this example, mice with prominent growth status and healthy physique were selected as experimental objects, which were purchased from Huafukang Biotechnology Co., Ltd. The mice were cheap, easily and widely available, and easy to raise, came from the inbred strain C57/B6J, and had a body weight of 20 g to 30 g and a high degree of standardization, which was convenient for administration and sampling. Male mice were preferred, which were robust and in line with the characteristic that anti-PD1 mAb-induced autoimmune myocarditis is more common among males, such that test errors due to insufficient physical activity could be avoided as much as possible during a test process.

2.2 Raising Conditions

The experimental mice were raised at a temperature of 22° C. to 34° C. and a humidity of 40% to 70%. The experimental mice had free access to food and drinking water.

2.3 Modeling Process

120 SPE C57/BL6 male mice were raised adaptively for 1 week, during which a litter was changed every day, and a basic feed and purified water were provided.

The mice in the previous step were divided into 4 groups:

Group A: 30 mice: The mice were injected with 100 μl of PDL1 (CD274 gene)-overexpressing AAV9 through the tail vein, and 3 weeks later, an anti-PD1 mAb was injected intraperitoneally at 10 mg/kg once a week, 3 times in total.

Group B: 30 mice: The mice were injected with 100 μl of PDL1 (CD274 gene)-overexpressing AAV9 control through the tail vein, and 3 weeks later, an anti-PD1 mAb was injected intraperitoneally at 10 mg/kg once a week, 3 times in total.

Group C: 30 mice: The mice were injected intraperitoneally with an anti-PD1 mAb at 10 mg/kg once a week, 3 times in total.

Group D: 30 mice: The mice were injected intraperitoneally with IgG at 10 mg/kg once a week, 3 times in total. Then the mice were further raised with the basic feed and purified water.

After cardiac magnetic resonance and electrocardiogram acquisition were conducted once a week, 10 mice were sacrificed by cervical dislocation, and hearts were collected for HE staining.

2.4 Results

The cardiac pathology was used for determination, which was a gold standard for determining whether the model was successfully established.

Group A: After 1 injection, 10 mice were subjected to cardiac pathologic examination, 5 of which showed diffuse myofilament lysis of cardiomyocytes and T cell infiltration, had no T cells in the myocardium under physiological conditions, and did not die, indicating a modeling success rate of 50%. After 2 injections, 10 mice were subjected to cardiac pathologic examination, 8 of which showed diffuse myofilament lysis of cardiomyocytes and T cell infiltration, indicating a modeling success rate of 80%. After 3 injections, 10 mice were subjected to cardiac pathologic examination, all of which showed diffuse myofilament lysis of cardiomyocytes and T cell infiltration, indicating a modeling success rate of 100%.

Group B: After 1 injection, 10 mice were subjected to cardiac pathologic examination, 1 of which showed diffuse myofilament lysis of cardiomyocytes and cell infiltration, had no cells in the myocardium under physiological conditions, and did not die, indicating a modeling success rate of 10%. After 2 injections, 10 mice were subjected to cardiac pathologic examination, 4 of which showed diffuse myofilament lysis of cardiomyocytes and T cell infiltration, indicating a modeling success rate of 40%. After 3 injections, 10 mice were subjected to cardiac pathologic examination, 7 of which showed diffuse myofilament lysis of cardiomyocytes and T cell infiltration, and did not die, indicating a modeling success rate of 70%. The group B was milder than the group A.

Group C: After 1 injection, 10 mice were subjected to cardiac pathologic examination, 2 of which showed diffuse myofilament lysis of cardiomyocytes and T cell infiltration, had no T cells in the myocardium under physiological conditions, and did not die, indicating a modeling success rate of 20% After 2 injections, 10 mice were subjected to cardiac pathologic examination, 5 of which showed diffuse myofilament lysis of cardiomyocytes and T cell infiltration, indicating a modeling success rate of 50%. After 3 injections, 10 mice were subjected to cardiac pathologic examination, 6 of which showed diffuse myofilament lysis of cardiomyocytes and T cell infiltration, and did not die, indicating a modeling success rate of 60%. The group C was milder than the group A.

Group D: After 1 injection, 10 mice were subjected to cardiac pathologic examination, and normal results were obtained; after 2 injections, 10 mice were subjected to cardiac pathologic examination, and normal results were obtained; and after 3 injections, 10 mice were subjected to cardiac pathologic examination, and normal results were obtained.

The present disclosure has been described in detail above with reference to general descriptions and specific examples, but it will be apparent to those skilled in the art that some modifications or improvements can be made based on the present disclosure. Therefore, all these modifications or improvements made without departing from the spirit of the present disclosure fall within the scope of the present disclosure.

What is claimed is:

1. A method of making mouse that displays cardiomyocyte myofilament lysis, the method comprising administering:
   an adeno-associated virus 9 (AAV9) vector encoding programmed cell death ligand 1 (PDL-1) operably linked to a cTnT promoter to a mouse intravenously; and
   monoclonal antibody (mAb) that binds to programmed cell death ligand 1 (PDL-1) to the mouse intraperitoneally
such that the mouse displays cardiomyocyte myofilament lysis.

2. The method according to claim 1, wherein the mouse displays myocardial T-cell infiltration.

3. The method according to claim 1, wherein the mouse is male.

4. The method according to claim 1, wherein the PDL-1 is encoded by the nucleic acid sequence of SEQ ID NO: 1.

* * * * *

SEQUENCE LISTING

<160> NUMBER OF SEQ ID NOS: 3

<210> SEQ ID NO 1
<211> LENGTH: 873
<212> TYPE: DNA
<213> ORGANISM: Artificial Sequence
<220> FEATURE:
<223> OTHER INFORMATION: target gene

<400> SEQUENCE: 1

```
atgaggatat tgctggcat tatattcaca gcctgctgtc acttgctacg ggcgtttact        60
atcacggctc caaaggactt gtacgtggtg gagtatggca gcaacgtcac gatggagtgc       120
agattccctg tagaacggga gctggacctg cttgcgttag tggtgtactg ggaaaaggaa       180
gatgagcaag tgattcagtt tgtggcagga gaggaggacc ttaagcctca gcacagcaac       240 ttcagggga gagcctcgct gccaaaggac cagcttttga agggaaatgc tgcccttcag        300
atcacagacg tcaagctgca ggacgcaggc gtttactgct gcataatcag ctacggtggt       360
gcggactaca agcgaatcac gctgaaagtc aatgccccat accgcaaaat caaccagaga       420
atttccgtgg atccagccac ttctgagcat gaactaatat gtcaggccga gggttatcca       480
gaagctgagg taatctggac aaacagtgac caccaacccg tgagtgggaa gagaagtgtc       540
accacttccc ggacagaggg gatgcttctc aatgtgacca gcagtctgag ggtcaacgcc       600
acagcgaatg atgttttcta ctgtacgttt tggagatcac agccagggca aaaccacaca       660
gcggagctga tcatcccaga actgcctgca acacatcctc cacagaacag gactcactgg       720
gtgcttctgg atccatcct gttgttcctc attgtagtgt ccacggtcct cctcttcttg        780
agaaaacaag tgagaatgct agatgtggag aaatgtggcg ttgaagatac aagctcaaaa       840
aaccgaaatg atacacaatt cgaggagacg taa                                   873
```

<210> SEQ ID NO 2
<211> LENGTH: 45
<212> TYPE: DNA
<213> ORGANISM: Artificial Sequence
<220> FEATURE:
<223> OTHER INFORMATION: AAV-m-CD274-Nhe/Nhe-F primer

<400> SEQUENCE: 2

```
ttaatacgac tcactatagg ctagcgccac catgaggata tttgc                       45
```

<210> SEQ ID NO 3
<211> LENGTH: 45
<212> TYPE: DNA
<213> ORGANISM: Artificial Sequence
<220> FEATURE:
<223> OTHER INFORMATION: AAV-m-CD274-Nhe/Nhe-R primer

<400> SEQUENCE: 3

```
ccttgtagtc aagcttggtg ctagccgtct cctcgaattg tgtat                       45
```